US011471820B2

(12) United States Patent
Stuckert et al.

(10) Patent No.: US 11,471,820 B2
(45) Date of Patent: Oct. 18, 2022

(54) CHARACTERISTICS OF TUNABLE ADSORBENTS FOR RATE SELECTIVE SEPARATION OF NITROGEN FROM METHANE

(71) Applicants: Nicholas R. Stuckert, Grand Island, NY (US); Neil A. Stephenson, E. Amherst, NY (US); Philip A. Barrett, Tonawanda, NY (US); Steven J. Pontonio, Eden, NY (US)

(72) Inventors: Nicholas R. Stuckert, Grand Island, NY (US); Neil A. Stephenson, E. Amherst, NY (US); Philip A. Barrett, Tonawanda, NY (US); Steven J. Pontonio, Eden, NY (US)

(73) Assignee: PRAXAIR TECHNOLOGY, INC., Danbury, CT (US)

(*) Notice: Subject to any disclaimer, the term of this patent is extended or adjusted under 35 U.S.C. 154(b) by 198 days.

(21) Appl. No.: 17/034,831

(22) Filed: Sep. 28, 2020

(65) Prior Publication Data
US 2021/0008487 A1 Jan. 14, 2021

Related U.S. Application Data

(63) Continuation of application No. PCT/US2019/024594, filed on Mar. 28, 2019.
(Continued)

(51) Int. Cl.
*B01D 53/047* (2006.01)
*B01J 20/18* (2006.01)
(Continued)

(52) U.S. Cl.
CPC ....... *B01D 53/047* (2013.01); *B01D 53/0423* (2013.01); *B01J 20/18* (2013.01);
(Continued)

(58) Field of Classification Search
CPC ........ B01D 2253/108; B01D 2253/116; B01D 2253/25; B01D 2253/308; B01D 2256/10;
(Continued)

(56) References Cited

U.S. PATENT DOCUMENTS

| 2,843,219 A | 7/1958 | Habgood |
| 4,801,308 A | 1/1989 | Keefer |

(Continued)

FOREIGN PATENT DOCUMENTS

| CN | 105396420 A | 3/2016 |
| CN | 205575628 U | 9/2016 |

(Continued)

OTHER PUBLICATIONS

Ackley, M. W. et al., "Adsorption Characteristics of High-Exchange Clinoptilolites", Industrial & Engineering Chemistry Research, vol. 30, No. 12, Dec. 30, 1991, pp. 2523-2530, XP000274307, ISSN: 0888-5885, DOI: 10.1021/Ie00060A004 point "B. Pore Volume", p. 2527-2528, Figure 5.

(Continued)

*Primary Examiner* — Sharon Pregler
(74) *Attorney, Agent, or Firm* — Ralph J. Mancini

(57) ABSTRACT

The present invention generally relates to a pressure swing adsorption process for separating an adsorbate impurity from a feed stream comprising product gas, said process comprising feeding the feed stream to an adsorbent bed at a pressure of from about 60 psig to 2000 psig, wherein said adsorbent bed comprises adsorbent having:
An isosteric heat of adsorption of from about 5 kJ/mol to about 30 kJ/mol, as determined by the LRC method, for the adsorbate,
and an equivalent 65 kJ/mol or less isosteric heat of adsorption for the product,
wherein the adsorbent has a rate of adsorption for the adsorbate impurity that is at least 10 times greater than the
(Continued)

rate of adsorption for the product gas as determined by the TGA method and recovering said product gas with a reduced a level of said adsorbate impurity.

The invention also related to an adsorbent useful in PSA separations, particularly separating $N_2$ from methane, $CO_2$ from methane $O_2$ from $N_2$ and the like.

19 Claims, 5 Drawing Sheets

Related U.S. Application Data

(60) Provisional application No. 62/649,798, filed on Mar. 29, 2018.

(51) Int. Cl.
*C07C 7/12* (2006.01)
*C10L 3/10* (2006.01)
*B01D 53/04* (2006.01)

(52) U.S. Cl.
CPC ............... *B01J 20/186* (2013.01); *C07C 7/12* (2013.01); *C10L 3/105* (2013.01); *B01D 2253/108* (2013.01); *B01D 2256/10* (2013.01); *B01D 2256/16* (2013.01); *B01D 2256/245* (2013.01); *B01D 2257/102* (2013.01); *B01D 2257/104* (2013.01); *B01D 2257/504* (2013.01); *B01D 2259/404* (2013.01); *B01D 2259/40011* (2013.01); *B01D 2259/4062* (2013.01); *C10L 2290/542* (2013.01)

(58) Field of Classification Search
CPC .......... B01D 2256/16; B01D 2256/245; B01D 2257/102; B01D 2257/104; B01D 2257/504; B01D 2259/40011; B01D 2259/404; B01D 2259/4062; B01D 53/02; B01D 53/0423; B01D 53/047; B01J 20/18; B01J 20/186; C07C 7/12; C10L 2290/542; C10L 3/104; C10L 3/105; Y02C 20/40

See application file for complete search history.

(56) References Cited

U.S. PATENT DOCUMENTS

| | | |
|---|---|---|
| 4,816,121 A | 3/1989 | Keefer |
| 4,964,889 A | 10/1990 | Chao |
| 4,968,329 A | 11/1990 | Keefer |
| 5,082,473 A | 1/1992 | Keefer |
| 5,203,888 A | 4/1993 | Maurer |
| 5,256,172 A | 10/1993 | Keefer |
| 5,258,056 A | 11/1993 | Shirley et al. |
| 5,702,504 A | 12/1997 | Schaub et al. |
| 6,030,435 A | 2/2000 | Monereau et al. |
| 6,051,050 A | 4/2000 | Keefer et al. |
| 6,056,804 A | 5/2000 | Keefer et al. |
| 6,063,161 A | 5/2000 | Keefer et al. |
| 6,176,897 B1 | 1/2001 | Keefer |
| 6,197,092 B1 | 3/2001 | Butwell et al. |
| 6,231,644 B1 | 5/2001 | Jain et al. |
| 6,315,817 B1 | 11/2001 | Butwell et al. |
| 6,406,523 B1 | 6/2002 | Connor et al. |
| 6,444,012 B1 | 9/2002 | Dolan et al. |
| 6,629,525 B2 | 10/2003 | Hill et al. |
| 6,651,658 B1 | 11/2003 | Hill et al. |
| 6,691,702 B2 | 2/2004 | Appel et al. |
| 7,179,324 B2 | 2/2007 | Baksh et al. |
| 7,641,716 B2 | 1/2010 | Lomax, Jr. et al. |
| 8,778,051 B2 | 7/2014 | Weist, Jr. et al. |
| 9,381,460 B2 | 7/2016 | Weist, Jr. et al. |
| 2005/0098034 A1 | 5/2005 | Gittleman et al. |
| 2008/0028288 A1 | 11/2008 | Kelley et al. |
| 2008/0028289 A1 | 11/2008 | Deckman et al. |
| 2008/0282884 A1 | 11/2008 | Kelley et al. |
| 2008/0282892 A1 | 11/2008 | Deckman et al. |
| 2012/0174775 A1 | 7/2012 | Baksh et al. |
| 2014/0208797 A1 | 7/2014 | Kelley et al. |
| 2014/0373713 A1 | 12/2014 | Weist, Jr. et al. |
| 2017/0136405 A1* | 5/2017 | Ravikovitch ...... B01D 53/0476 |
| 2017/0173555 A1* | 6/2017 | Seo .................... B01J 20/28083 |
| 2018/0229175 A1 | 8/2018 | Pontonio et al. |

FOREIGN PATENT DOCUMENTS

| | | |
|---|---|---|
| EP | 2663382 B1 | 8/2017 |
| WO | 1999/032222 A1 | 7/1999 |
| WO | 2002/058818 A2 | 8/2002 |
| WO | 2008/005492 A1 | 1/2008 |
| WO | 2012/096812 A1 | 7/2012 |
| WO | 2019/191436 A1 | 10/2019 |

OTHER PUBLICATIONS

Mehrotra, et al., Arithmetic Approach for Complex PSA Cycle Scheduling, Adsorption, 2010, pp. 113-126, vol. 16, Springer Science+Business Media.

Yon and Turnock, Multicomponent Adsorption Equilibria on Molecular Sieves, published as part of the AIChE Symposium Series, 117, vol. 67, in 1971 in Adsorption Technology.

Gamba, Giuseppe et al., "Adsorbed Solution Theory Models for Multicomponent Adsorption Equilibria", AIChE Journal, Jun. 1989, vol. 35, No. 6, pp. 959-966.

\* cited by examiner

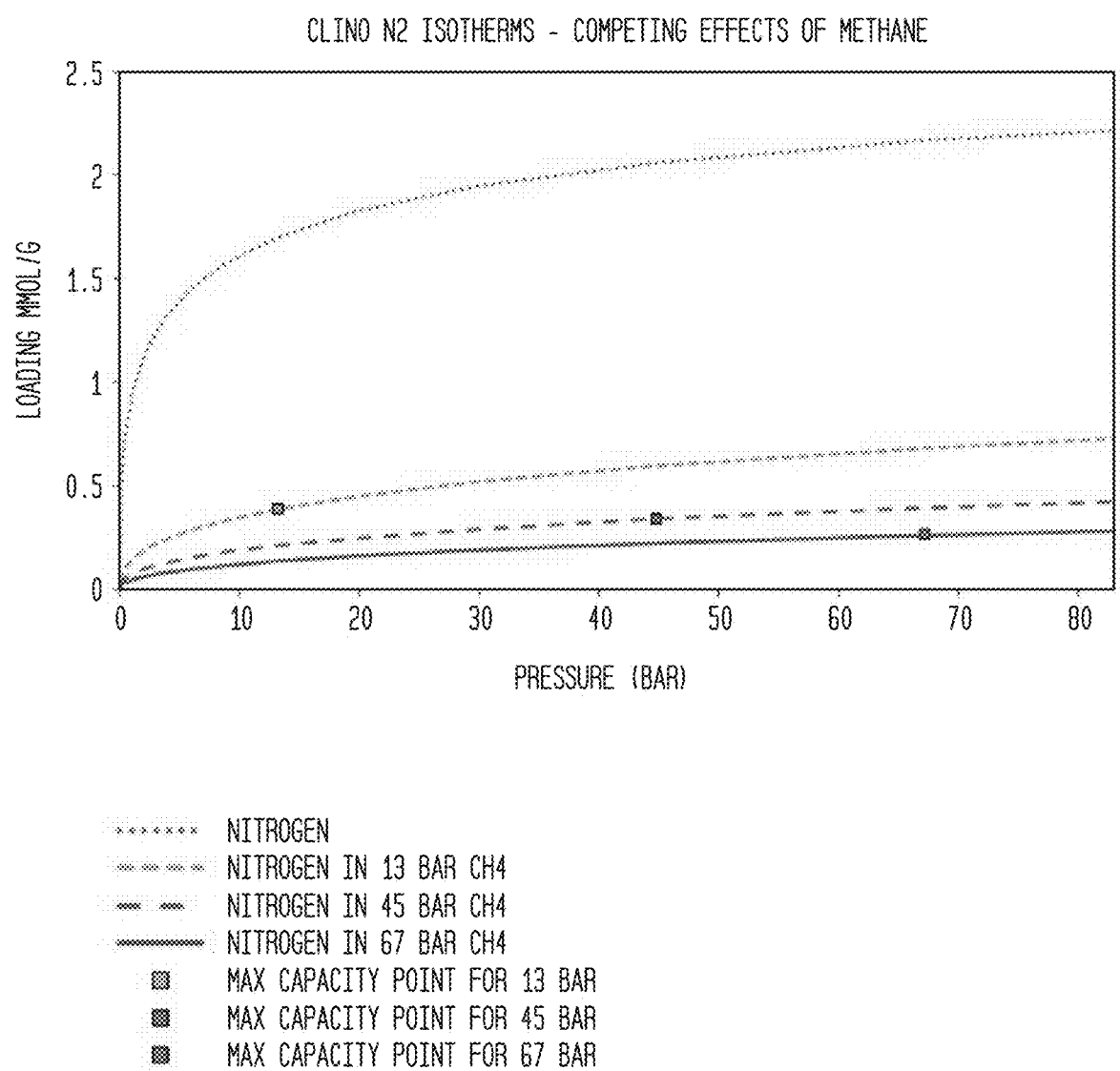

FIG. 3

```
METHOD LOG:
1:SELECT GAS: 1
2:RAMP 1.00°C/MIN TO 25.00°C
3:ISOTHERMAL FOR 20.00 MIN
4:SAMPLING INTERVAL 0.50 SEC/PT
5:SELECT GAS: 2
6:ISOTHERMAL FOR 30.00 MIN
7:SELECT GAS: 1
8:ISOTHERMAL FOR 30.00 MIN
9:SAMPLING INTERVAL 10.00 SEC/PT
10:RAMP 2.00°C/MIN TO 150.00°C
11:ISOTHERMAL FOR 60.00 MIN
12:RAMP 5.00°C/MIN TO 350.00°C
13:ISOTHERMAL FOR 120.00 MIN
14:RAMP 5.00°C/MIN TO 25.00°C
15:ISOTHERMAL FOR 120.00 MIN
16:SAMPLING INTERVAL 0.50 SEC/PT
17:SELECT GAS: 2
18:ISOTHERMAL FOR 30.00 MIN
19:SELECT GAS: 1
20:ISOTHERMAL FOR 30.00 MIN
21:END OF METHOD
```

CHARACTERISTICS OF TUNABLE ADSORBENTS FOR RATE SELECTIVE SEPARATION OF NITROGEN FROM METHANE

RELATED APPLICATIONS

This continuation-in-part application of and claims benefit to International Application No. PCT/US2019/024594, filed on Mar. 28, 2019, which claims benefit of U.S. Provisional Application Ser. No. 62/649,798, filed on Mar. 29, 2018, which are both incorporated herein by reference.

FIELD OF THE INVENTION

Separating nitrogen and methane has historically presented a challenge. While carbon-based adsorbents are readily available to adsorb methane from nitrogen, these leaves the methane at ambient pressure while the nitrogen is produced near the feed pressure. Typically, the methane is required at the feed pressure and the nitrogen at ambient pressure. It is then preferred to adsorb the nitrogen. The present invention generally relates to adsorbent characteristics used in a process to separate nitrogen from methane. The adsorbents are characterized by a moderate strength isosteric or heat of adsorption of nitrogen and methane. These material characteristics are used in a pressure swing adsorption (PSA) process, in order to adsorb the nitrogen and allow the methane to pass through the adsorption bed at or around the feed pressure.

BACKGROUND OF THE INVENTION

Since nitrogen adsorption from methane is a relatively unexplored area, it is important to draw the background from similar adsorption processes such as pressure swing adsorption (PSA), vacuum swing adsorption (VSA) and vacuum pressure swing (VPSA) which have been commercially utilized for bulk air separation, as well as trace air contaminant removal, for many decades. In PSA and VPSA processes, compressed air is pumped through a fixed bed of an adsorbent exhibiting an adsorptive preference for one of the main constituents, typically Na in bulk air separation, $CO_2$ and $H_2O$ in air prepurification, or CO and $CO_2$ in $H_2$ purification, etc., whereby an effluent product stream enriched in the lesser-adsorbed constituent is obtained. Improvements in these processes remain important goals, one principal means of which is the discovery and development of better process cycles. Significant improvements have been achieved in not only recovery of gas but also reductions in overall system size. These improvements also continue to provide important benefits even while the adsorbent being used in conjunction with the system is constantly improved and replaced with better alternatives.

A large majority of processes operate through the equilibrium adsorption of the gas mixture and kinetic separations have lately attracted considerable attention with the development of functional microporous adsorbents and efficient modeling tools. Still, relatively few steric separation processes have been commercialized. Kinetically based separation involves differences in the diffusion rates of different components of the gas mixture and allows different molecular species to be separated regardless of similar equilibrium adsorption parameters. Kinetic separations often utilize carbon molecular sieves as the adsorbent since they exhibit a distribution of pore sizes which allow the different gaseous species to diffuse into the adsorbent at different rates while avoiding exclusion of any component of the mixture. Kinetic separations can be used for the separation of industrial gases, for example, for the separation of nitrogen from air and argon from other gases. In the case of the nitrogen/oxygen separation (for example, oxygen and nitrogen differ in size by only 0.02 nm), the separation is efficient since the rate of transport of oxygen into the carbon sieve pore structure is markedly higher than that of nitrogen. Hence, the kinetic separation works, even though the equilibrium loading levels of oxygen and nitrogen are virtually identical.

Kinetically based separation processes may be operated, as noted in U.S. Patent Application Publication No. 2008/0282884, as pressure swing adsorption (PSA), temperature swing adsorption (TSA), partial pressure swing or displacement purge adsorption (PPSA) or as hybrid processes comprised of components of several of these processes. These swing adsorption processes can be conducted with rapid cycles, in which case they are referred to as rapid cycle thermal swing adsorption (RCTSA), rapid cycle pressure swing adsorption (RCPSA), and rapid cycle partial pressure swing or displacement purge adsorption (RCPPSA) technologies, with the term "swing adsorption" taken to include all of these processes and combinations of them.

The faster the beds perform the steps required to complete a cycle, the smaller the beds can be when used to process a given hourly feed gas flow. Several other approaches to reducing cycle time in PSA processes have emerged which use rotary valve technologies (U.S. Pat. Nos. 4,801,308; 4,816,121; 4,968,329; 5,082,473; 5,256,172; 6,051,050; 6,063,161; 6,406,523; 6,629,525; 6,651,658; and 6,691,702). A parallel channel (or parallel passage) contactor with a structured adsorbent may be used to allow for efficient mass transfer in these rapid cycle pressure swing adsorption processes. Approaches to constructing parallel passage contactors with structured adsorbents are known (U.S. Patent Application Publication No. 2008/0282892).

In the case of kinetic-controlled PSA processes, the adsorption and desorption are more typically caused by cyclic pressure variation, whereas in the case of TSA, PSA and hybrid processes, adsorption and desorption may be caused by cyclic variations in temperature, partial pressure, or combinations of pressure, temperature and partial pressure, respectively. In the exemplary case of PSA, kinetic-controlled selectivity may be determined primarily by micropore mass transfer resistance (e.g., diffusion within adsorbent particles or crystals) and/or by surface resistance (e.g., narrowed micropore entrances). For successful operation of the process, a relatively and usefully large working uptake (e.g., the amount adsorbed and desorbed during each cycle) of the first component and a relatively small working uptake of the second component may preferably be achieved. Hence, the kinetic-controlled PSA process requires operation at a suitable cyclic frequency, balancing the avoidance of excessively high cycle frequency where the first component cannot achieve a useful working uptake with excessively low frequency where both components approach equilibrium adsorption values.

Some established kinetic-controlled PSA processes use carbon molecular sieve adsorbents, e.g., for air separation with oxygen comprising the first more-adsorbed component and nitrogen the second less adsorbed component. Another example of kinetic-controlled PSA is the separation of nitrogen as the first component from methane as the second component. Those may be performed over carbon molecular sieve adsorbents or more recently employing a hybrid kinetic/equilibrium PSA separation (principally kinetically based but requiring thermal regeneration periodically due to partial equilibrium adsorption of methane on the adsorbent material) over titanosilicate based adsorbents such as ETS-4 (U.S. Pat. Nos. 6,197,092 and 6,315,817). Thermal regeneration is described as the method of passing heated gas across the adsorbent bed in order to cause desorption of the methane. This would typically take more than 24 hours during which point more beds would be required to continue operation or a second system would need to be in place. Both of these methods add considerable cost to the system and a method to eliminate thermal regeneration would have substantial economic benefit.

Zeolite adsorbents for the removal of nitrogen from a natural gas are also known. U.S. Pat. No. 2,843,219 discloses a process for removing nitrogen from natural gas utilizing zeolites broadly and contains specific examples for the use of solid phase molecular sieve materials of which zeolite 4A is noted as suitable for the intended separation. The '219 patent does not disclose a pressure swing adsorption process, but rather discloses a process where the molecular sieve adsorbent is regenerated by thermal swing. However, the process disclosed in this patent did not achieve commercial success as TSA processes for bulk separation are rarely practical and this did not provide a cost efficient method for the separation of nitrogen from natural gas. TSA operation is essentially the same process as the thermal regeneration described for ETS-4, except done more frequently and done as the primary method for regenerating the adsorbent.

Another patent utilizing molecular sieves for the removal of nitrogen from natural gas is U.S. Pat. No. 4,964,889 which discloses the use of a clinoptilolites zeolite containing magnesium cations for the removal of nitrogen. These zeolites also periodically require thermal regeneration to perform similar to ETS-4.

SUMMARY OF THE INVENTION

The present invention generally relates to a pressure swing adsorption process for separating an adsorbate impurity from a feed stream comprising product gas, said process comprising feeding the feed stream to an adsorbent bed at a pressure of from about 60 psig to 2000 psig, wherein said adsorbent bed comprises adsorbent having:

An isosteric heat of adsorption of from about 5 kJ/mol to about 25 kJ/mol, as determined by the LRC method, for the adsorbate, and a isosteric heat of adsorption for any gas species in the product that is 50-200% of isosteric heat of adsorption of the adsorbate, wherein the adsorbent has a rate of adsorption for the adsorbate impurity that is at least 5 times greater than the rate of adsorption for the product gas as determined by the Hiden method and recovering said product gas with a reduced a level of said adsorbate impurity. The invention also relates to an adsorbent useful in PSA separations, particularly separating $N_2$ from methane, $CO_2$ from methane $O_2$ from $N_2$ and the like.

DETAILED DESCRIPTION OF THE FIGURES

FIG. 1 shows the effect of competing adsorption vs. pressure on a 50/50 mixture of $CH_4$ and $N_2$ under saturation of both components on 4A. The maximum working capacity peaks around 40 bar but is relatively flat over the range of 10-70 bar. These isotherms are based on the LRC approximation.

FIG. 2 shows the effect of competing adsorption vs. pressure on a 50/50 mixture of $CH_4$ and $N_2$ under saturation of both components on Clinoptilolite. The maximum working capacity peaks at less than 10 bar and significantly decreases with increasing pressure. These isotherms are based on the pure component loading ratio correlation (LRC) approximation (see "Multicomponent Adsorption Equilibria on Molecular Sieves" by Yon and Turnock, published as part of the AIChE Symposium Series, 117, Vol. 67, in 1971 in Adsorption Technology, or Yang, Gas Separation by Adsorption Processes, 1987, ISBN 9781483162669).

FIG. 3 outlines the TGA method sequence to screen the relative rates of nitrogen on candidate adsorbents.

DETAILED DESCRIPTION OF THE INVENTION

Figure 1:
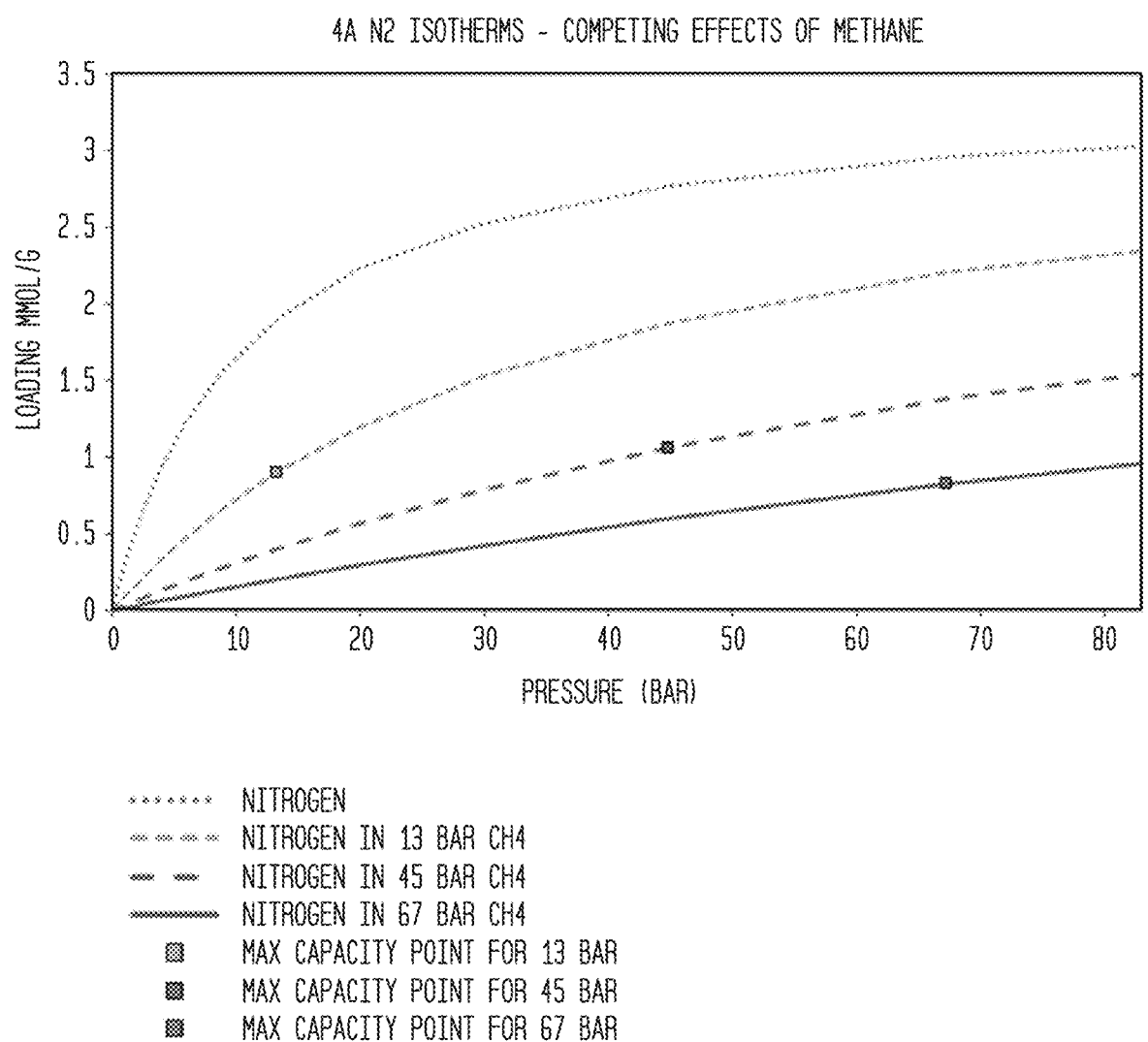

Known adsorbents for kinetically controlled PSA processes include clinoptilolite, ETS-4 (barium exchanged titano-silicate) and the like. Both clinoptilolite and ETS-4 required thermal regeneration due to the strength of adsorption of methane. An objective of the present invention is to eliminate the costly thermal regeneration and to decrease the bed size, by creating and using an adsorbent with characteristics of lower isosteric heat of adsorption compared with state-of-the-art materials ETS-4 and clinoptilolite.

The literature regarding state-of-the-art materials such as ETS-4 do not identify the requirements for isosteric heat of adsorption for the contaminants or the products when attempting to separate, as an example, nitrogen from methane in a kinetically controlled process. ETS-4 has a relatively high isosteric heat of adsorption for both nitrogen and methane. This causes methane to increasingly adsorb over time and block the adsorption sites from nitrogen thereby reducing the adsorbent capacity and the effectiveness of the system as a whole.

One conventional solution to this problem is to use thermal regeneration even in 100-200 psig pressure cycles. According to Mehrotra, et al. and conventional wisdom for equilibrium separations, an adsorbent that has an isosteric heat of adsorption near the maximum acceptable is the preferred adsorbent for rate-based separations. ETS-4 fits this conventional wisdom, however the finding here is that an adsorbent with a substantially reduced isosteric heat of adsorption not only performs as well as ETS-4, it also is more stable over time and does not require thermal regeneration.

The present inventors have unexpectedly found that a substantial reduction in the isosteric heat of adsorption of 20% or more is preferred and leads to elimination of thermal regeneration while maintaining production and product purity. More specifically, tunable zeolites based on 4A made in accordance with the teachings of U.S. Patent Application No. 20180229175, which is incorporated herein in its entirety, were modified to illustrate the isosteric heat of adsorption characteristics that are required to eliminate costly thermal regeneration and the possible heats of adsorption that are achievable with rate selective tunable zeolites and mixtures of moderate strength cations ($Na^+$, $K^+$) to enable their use in higher pressure processes. These heats of adsorption, from generally about 5 kJ/mol to about 25 kJ/mol define the adsorbent properties for nitrogen adsorption from natural gas in a rate selective process and can extend up to 40 kJ/mol for lower pressure (<100 psig) applications. The desirable characteristics for an adsorbent are defined as:
1. A isosteric heat of adsorption as determined by isotherm measurements fit with the LRC method show that a isosteric heat of adsorption (i.e. −A2)>5 kJ/mol and <30 kJ/mol is preferred and in another embodiment <25 kJ/mol.
2. The rate of uptake of nitrogen that is 5× greater than methane as determined by the Hiden gravimetric method at going from vacuum to 1 Bar pressure of >99.9% Nitrogen (less than 0.1 ppm $H_2O$) at 35° C. for nitrogen measurements and vacuum to 1 Bar pressure of >99.9% Methane (less than 0.1 ppm $H_2O$) at 35° C. for methane measurements.

Preferred characteristics also include:
1. An isosteric heat of adsorption of methane that is <200% but greater than 50% that of nitrogen and preferably <125% but greater than 50% of that of nitrogen.
2. The total adsorption capacity as determined by gravimetric measurements using a Hiden pressure microbalance, following activation at 350 to 400° C. under vacuum, that are allowed up to one week to equilibrate is preferably >0.2 wt % and most preferably >0.7 wt % in a 1 Bar environment of >99.9% nitrogen at 35° C.

While these characteristics are primarily described for the separation of nitrogen from natural gas, it should be noted that they will apply to other kinetic based separations as well provided that the impurity to be separated from the product gas has the characteristics described for nitrogen and natural gas/methane, respectively. More specifically, the adsorbate impurity should have an isosteric heat of adsorption as determined by isotherm measurements fit by LRC method of >10 kJ/mol and <30 kJ/mol, in another embodiment <25 kJ/mol. The rate of uptake of said adsorbate should also be 5× greater than that of the product gas as determined by the Hiden gravimetric method going from vacuum to 1 Bar pressure of >99.9% Nitrogen (less than 0.1 ppm $H_2O$) at 35° C. for nitrogen measurements and going from vacuum to 1 Bar pressure of >99.9% Methane (less than 0.1 ppm $H_2O$) at 35° C. for methane measurements.

The process may also include other adsorbents to remove a range of contaminants that are present in the feed stream including hydrocarbons that contain more than 4 carbon atoms, moisture, carbon dioxide, sulfur containing species or other species that may reduce the working capacity of the adsorbent described herein. In one embodiment the PSA process is directed to the separation of $N_2$ from methane, in another embodiment the separation of $CO_2$ from methane, and in yet another embodiment $O_2$ from $N_2$. Other separations are apparent to those skilled in the art. In the event that one of these adsorbents fails to remove the species, thermal regeneration may be performed to remove that species from the adsorbent described and still fall within the realm of this invention which is to eliminate thermal regeneration from being used to remove the product gas of the invention.

In addition to tunable 4A adsorbents, other adsorbents having crystalline inorganic frameworks can be utilized in accordance with the present invention. Crystalline inorganic adsorbents are defined as any microporous aluminosilicate having a regular arrangement of atoms in a space lattice. Zeolites are a preferred crystalline inorganic framework. Zeolites are porous crystalline aluminosilicates which comprise assemblies of $SiO_4$ and $AlO_4$ tetrahedra joined together through sharing of oxygen atoms. The general stoichiometric unit cell formula for a zeolite framework is:

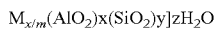

$$M_{x/m}(AlO_2)x(SiO_2)y]zH_2O$$

where M is the cation with a valence of m, z is the number of water molecules in each unit cell, and x and y are integers such that y/x is greater than or equal to 1. The ratio of oxygen atoms to combined aluminum and silicon atoms is equal to 2. Therefore, each aluminum atom introduces a negative charge of one (−1) on the zeolite framework which is balanced by that of a cation. To activate the zeolite the water molecules are completely or substantially removed by raising the temperature or pulling vacuum. This results in a framework with the remaining atoms intact producing cavities connected by channels or pores. The channel size is determined by the number of atoms which form the apertures leading to the cavities as well as cation type and position. Changing the position and type of the cation allows one to change and fine tune channel size and the properties of the zeolite, including its selectivity. For instance, the sodium form of Zeolite A has a pore size of ~4 Å and is called a 4A molecular sieve. If at least 40% of the sodium ions are exchanged with a larger potassium ion, the pore size is reduced to ~3 Å. If these are exchanged with >70% calcium, one calcium ion replaces two sodium ions and the pore opening is increased to ~5 Å. The ability to adjust pores to precisely determine uniform openings allows for molecules smaller than its pore diameter to be adsorbed while excluding larger molecules. The Si/Al ratio can also be varied to modify the framework structure and provide selectivity required for a given separation. This is why zeolites, known as molecular sieves, are very effective in separating on the basis of size.

Some non-limiting examples of zeolites that can be employed in the context of the invention include zeolite A, chabazite, mordenite, clinoptilolite, ZSM-5, or combinations thereof. The above zeolites can be exchanged with cations including Li, Na, K, Mg, Ca, Sr, Ba, Cu, Ag, Zn, NH4+ and mixtures thereof. In one embodiment zeolite 4A is the adsorbent of choice.

In its broadest embodiment the invention is directed to a PSA process for separating an adsorbate impurity from a feed stream comprising product gas, said process comprising feeding the feed stream to an adsorbent bed at a pressure of from about 60 psig to 2000 psig, wherein said adsorbent bed comprises adsorbent having:
i. An isosteric heat of adsorption of from about 5 kJ/mol to about 25 kJ/mol, as determined by the LRC method, for the adsorbate, and
ii. an isosteric heat of adsorption for the product that is 50% to about 200% of the adsorbent's isosteric heat of adsorption for said adsorbate, wherein the adsorbent has a rate of adsorption for the adsorbate impurity that is at least 10 times greater than the rate of adsorption for the product gas as determined by the Hiden gravimetric method and recovering said product gas with a reduced level of said adsorbate impurity.

In another embodiment the invention is directed to a PSA process for separating $N_2$ from a methane gas feed stream said process comprising feeding the methane gas feed stream to an adsorbent bed at a pressure of from about 60 psig to 2000 psig, wherein said adsorbent bed comprises adsorbent having:
i. An isosteric heat of adsorption of from about 5 kJ/mol to about 25 kJ/mol, as determined by the LRC method, for the $N_2$ adsorbate, and
ii. an isosteric heat of adsorption for the methane product that is 50% to about 200% of the adsorbent's isosteric heat of adsorption for $N_2$, wherein the adsorbent has a rate of adsorption for the $N_2$ adsorbate that is at least 10 times greater than the rate of adsorption for the product methane gas as determined by the Hiden gravimetric method and recovering said methane product gas with a reduced level of said $N_2$ adsorbate impurity.

In another embodiment the invention is directed to a PSA process for separating $CO_2$ from a methane gas feed stream said process comprising feeding the methane gas feed stream to an adsorbent bed at a pressure of from about 60 psig to 2000 psig, wherein said adsorbent bed comprises adsorbent having:
  i. An isosteric heat of adsorption of from about 5 kJ/mol to about 25 kJ/mol, as determined by the LRC method, for the $CO_2$ adsorbate, and
  ii. an isosteric heat of adsorption for the methane product that is 50 to about 200% of the adsorbent's isosteric heat of adsorption $CO_2$,
wherein the adsorbent has a rate of adsorption for the $CO_2$ adsorbate that is at least 10 times greater than the rate of adsorption for the product methane gas as determined by the Hiden gravimetric method and recovering said methane product gas with a reduced a level of said $CO_2$ adsorbate impurity.

In yet another embodiment the invention is directed to a PSA process for separating $O_2$ from a $N_2$ gas feed stream said process comprising feeding the $N_2$ gas feed stream to an adsorbent bed at a pressure of from about 60 psig to 2000 psig, wherein said adsorbent bed comprises adsorbent having:
  i. An isosteric heat of adsorption of from about 5 kJ/mol to about 25 kJ/mol, as determined by the LRC method, for the $O_2$ adsorbate, and
  ii. an equivalent heat of adsorption for the methane product that is from about 50% to about 200% of the adsorbent's isosteric heat of adsorption for the $O_2$ adsorbate,
wherein the adsorbent has a rate of adsorption for the $O_2$ adsorbate that is at least 10 times greater than the rate of adsorption for the product $N_2$ gas as determined by the Hiden gravimetric method and recovering said $N_2$ product gas with a reduced a level of said $O_2$ adsorbate impurity.

Finally, the invention relates to an adsorbent for PSA based separations, wherein said adsorbent has a isosteric heat of adsorption of from about 5 kJ/mol to about 25 kJ/mol, as determined by the LRC method, for the adsorbate impurity to be separated from the product containing feed gas stream, and an isosteric heat of adsorption for the product that is 50 to about 100% of the adsorbent's isosteric heat of adsorption for the adsorbate, wherein the adsorbent has a rate of adsorption for the adsorbate impurity that is at least 10 times greater than the rate of adsorption for the product gas as determined by the Hiden gravimetric method and recovering said product gas with a reduced a level of said adsorbate impurity. In one embodiment the tunable adsorbent is employed in a PSA process for the separation of $N_2$ from methane, in another embodiment the separation of $CO_2$ from methane, and in yet another embodiment the separation of $O_2$ from $N_2$.

The feed stream utilized in the PSA process of the invention may also contain additional gas species such as ethane, propane, butane and hydrocarbons with more than 4 carbon atoms, water, carbon dioxide or sulfur species and may include adsorbents to remove said hydrocarbons. These adsorbents could comprise activated carbon, silica, alumina, zeolites, titanosilicates, iron based, amine containing adsorbents or mixtures thereof. Typically, silica and alumina adsorbents are used for initial water removal, followed by zeolites. Typically, titanosilicates, zeolites, activated carbon, amine containing, or iron-based adsorbents are used for sulfur removal. Typically, zeolites, titanosilicates, activated carbon, silica or amine containing adsorbents are used for carbon dioxide removal. Typically, silica gel or activated carbon are used for hydrocarbon removal.

The following exemplary descriptions are provided for enablement purposes.

LRC Description

Adsorbents were characterized using the loading ratio correlation (LRC) method as described herein and based on the article "Multicomponent Adsorption Equilibria on Molecular Sieves" by Yon and Turnock, published as part of the AIChE Symposium Series, 117, Vol. 67, in 1971 in Adsorption Technology. Isotherm measurements were performed by using an IGA balance as described below, for temperatures of 20° C., 35° C. and 50° C.

IGA Description (Rate and Equilibrium)

Rate and equilibrium characterization of samples were performed using a Hiden IGA pressure microbalance (Model #HAS022650) which measures single component gas uptake and typical adsorption uptakes are performed using oxygen, nitrogen, carbon dioxide, carbon monoxide, helium, methane, and argon. Operating pressures vary from vacuum to 11 bar. This system was used to examine the adsorption of $N_2$ and $CH_4$. The samples were loaded and gas adsorptions were measured as instructed in the IGA Systems User Manual #HA-085-060. Each sample was loaded and activated in situ under vacuum with a temperature ramp of 0.7 C/min to between 350 and 400° C. and held for 12 hours. It was then cooled to the adsorption test temperature at a rate of 1° C./min. The amount of gas adsorbed by the adsorbent is measured in micrograms at a fixed temperature controlled by a constant temperature bath. The pressures points are taken from 0.1 bar to 10 Bar allowing up to 7 days to reach equilibrium. Equilibrium and leak check verification is done by a desorption isotherm that matches the adsorption isotherm. A buoyancy correction was determined using helium and this was used to adjust the microgram weight for buoyancy effects using the molecular weight of the gas being measured. The buoyancy corrected microgram weight was used to calculate uptake using standard methods and using the activated sample weight. For rate measurements, the test gas ($N_2$ or $CH_4$) was introduced at 1 Bar then the sample was held at pressure recording the weight as a function of time. System dynamics require approximately 2 minutes to stabilize. Weight data after 2 minutes were corrected for buoyancy and converted to uptakes in weight % or mmol/g and the uptake versus time data were fit to a first order process to obtain rates. Each material was tested first for $N_2$, prior to being reactivated before repeating the test using $CH_4$.

Breakthrough Description

A breakthrough test system was created to test the adsorbent samples using a 12" long 1" pipe filled with adsorbent. A breakthrough test was run by first saturating the bed with a flow of 300 sccm at 400 psig of 99% methane (where methane is >99.99%) and 1% helium (where helium is >99.99%) gas for 2 hours, then a flow of 300 sccm of a 49.75/49.75/0.5 mixture of $N_2$ (where nitrogen is >99.99%)/$CH_4$/He was introduced as a feed gas to the adsorbent bed and the outlet gas was measured using a gas chromatography mass spectrometer. The breakthrough was recorded as a nitrogen breakthrough example. After 30 minutes this flow was switched to 300 sccm of 99% nitrogen and 1% helium and held for 2 hours. Then the flow was switched back to the 300 sccm of 49.75/49.75/0.5 mixture of $N_2/CH_4$/He and this was recorded as the methane breakthrough. These breakthrough curves were then used with gPROMS software provided by Process Systems Enterprise, Inc. (PSE) to automatically perform parameter estimation of a model that was created as a replica of the system. The libraries supplied with the adsorption aspect of Process Builder from PSE are sufficient to replicate these results. A detailed description and instructions on how to perform these simulations is provided by PSE.

Modeling Description

The results from the breakthrough test and parameters obtained from the modeling were used with the methodology described by Mehrotra, et al. in Arithmetic Approach for Complex PSA Cycle Scheduling, Adsorption, 2010, pp. 113-126, vol. 16, Springer Science+Business Media which details the basis for modeling PSA processes. These simulations were performed using Process Builder, from PSE.

TGA Description

Routine characterization of tunable 4A samples for nitrogen rate screening was performed using a thermogravimetric method using a TA Instruments Q500 system installed in a glove box to minimize the impact of air leaks. A low volume furnace is required to properly measure the rate of uptake of gases. Nitrogen and oxygen gases supplied to the instrument were high purity. The balance purge gas and gas 1 was nitrogen and a gas 2 corresponds to oxygen for determination of nitrogen rates. For all experiments, a balance purge of 5 cc/minute was used and the gas directly over the sample was set to 95 cc/minute (nitrogen or oxygen). A sampling frequency of 0.5 sec/point was used for all adsorption steps. Alumina pans were used for all studies and the sample size after activation was in the range 100 to 120 mg.

Figure 4:
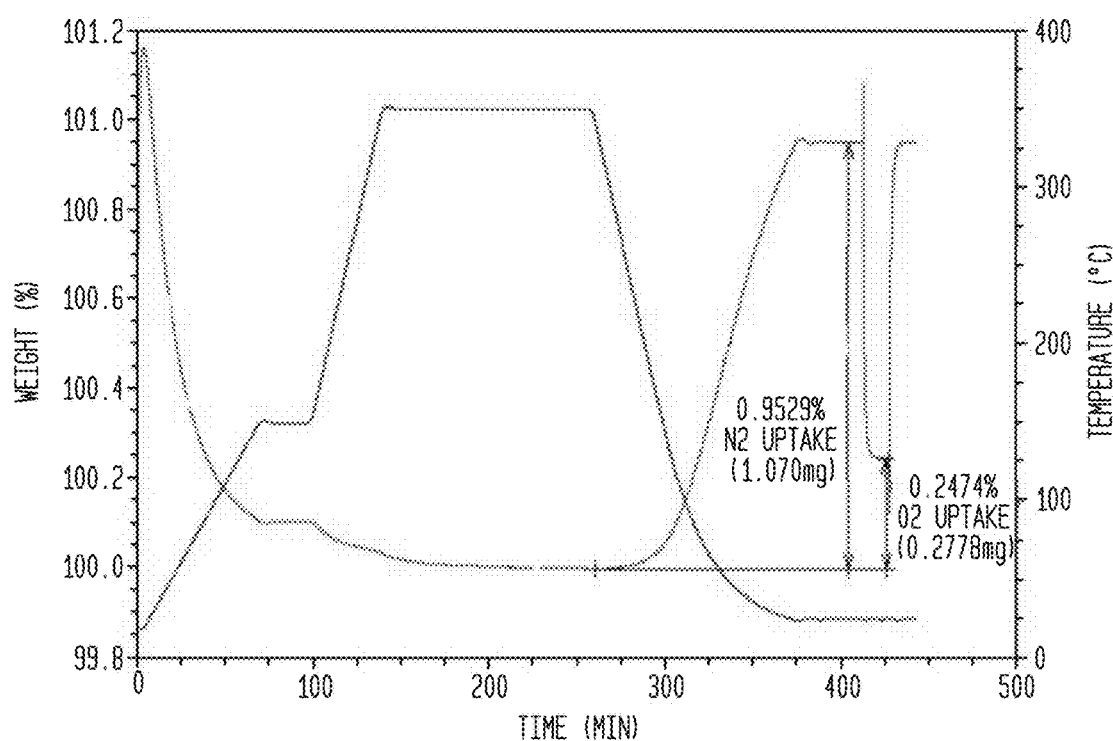
FIG. 4 shows an example of a TGA plot that is obtained following the method outlined in FIG. 3.
Figure 5:
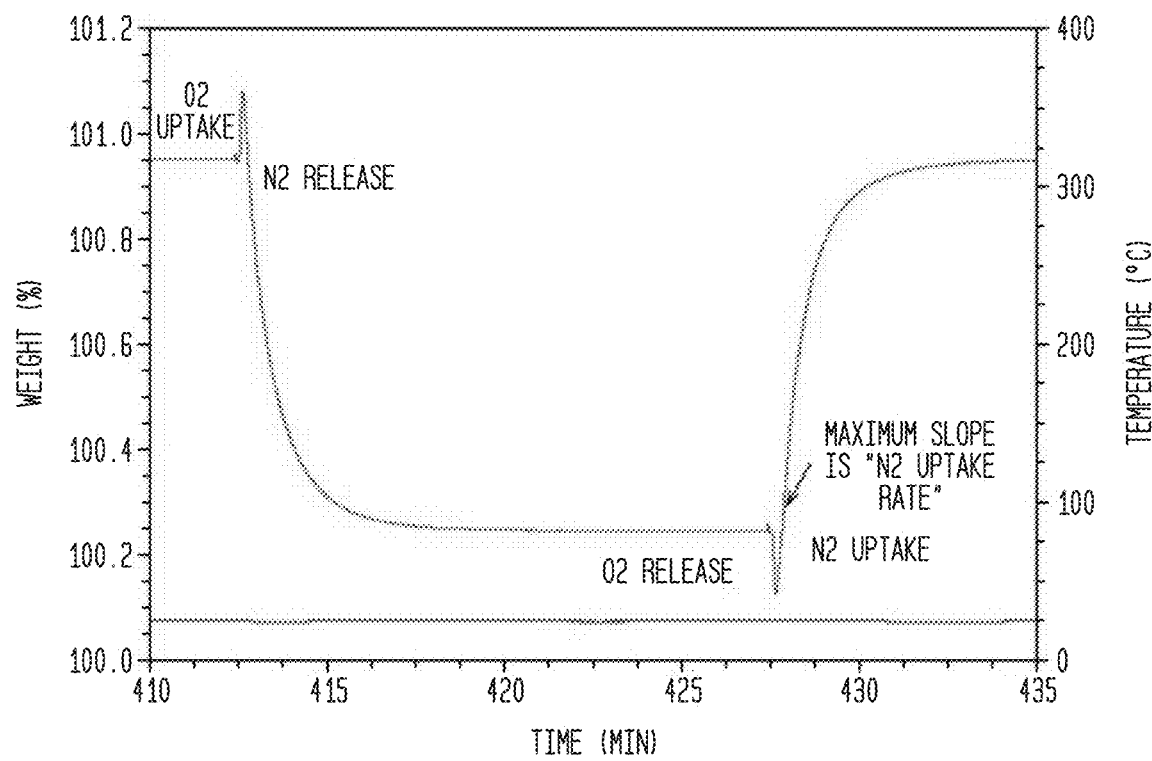
FIG. 5 shows an expansion of the same plot in FIG. 3 to illustrate the features observed during gas switching.

The TGA method (outlined in FIG. 3) involves both an in-situ activation step followed by adsorption tests using oxygen and nitrogen at 25° C. The sample activation was performed by heating the sample under nitrogen purge at 2° C. per minute to 150° C., maintaining isothermal for 60 minutes, heating at 5° C./minute to 350° C., holding at 350° C. for 120 minutes, then cooling to 25° C. The nitrogen equilibrium capacity at atmospheric pressure and 25° C. is reported as the weight gain on cooling under nitrogen relative to the minimum weight at 350° C. (the activated sample weight). An assessment of relative rate for nitrogen with different samples and preparation is captured by switching from nitrogen to oxygen. A transient weight gain is observed followed by a drop attributable to oxygen uptake followed by nitrogen leaving. A corresponding switch from oxygen back to nitrogen results in a transient weight loss followed by a weight gain attributable to oxygen loss followed by nitrogen pickup. Values reported as "nitrogen uptake rate" correspond to the maximum slope observed in the nitrogen uptake portion and is equivalent also to the peak in the derivative weight with respect to time for the same step as seen in FIGS. 4 and 5. Values are reported in weight %/minute.

Example 1. Moderately strong adsorbing sites—Moderate Heats of Adsorption for nitrogen (<25 kJ/mol) and methane (<50 kJ/mol) leads to weak competing adsorption from methane which can be used to avoid thermal regeneration and still maintain similarly high levels of product produced per amount of adsorbent used. As shown in FIG. 1, compared with a natural clinoptilolite adsorbent shown in FIG. 2 that loses 80-90% of equilibrium capacity for the nitrogen component due to competing adsorption with methane, the tunable zeolite 4A system loses only 50-60% of equilibrium capacity due to competing adsorption. Without desaturation methods, tunable zeolite 4A is able to continually produce a high purity product at moderate recoveries. This eliminates desaturation methods and significantly simplifies the system leading to a large reduction in capital and operating expense.

Method for Manufacturing Adsorbent:

23.00 lbs. of zeolite 4A powder supplied by Jianlong (as 4A-D) on a dry weight basis (29.50 lbs. wet weight) was placed in a WAM MLH50 plow mixer. With the mixer agitating, 2.16 lbs of MR-2404 (a solventless silicone containing silicone resin from Dow Corning) was pumped in at rate of 0.07 lb/min. After the MR-2404 addition was completed, 9.2 lbs of water was added at a rate of 0.3 lb/min under constant stirring in the plow mixer. At the end of the water addition, plow mixing was continued for an additional 5 minutes. The plow mixed powder product labeled hereinafter "the formulation" was transferred to a tilted rotating drum mixer having internal working volume of ~75 L and agitated therein at a speed of 24 rpm. Mixing of the formulation was continued while beads were gradually formed which had a porosity, as measured using a Micromeritics Autopore IV Hg porosimeter on the calcined product, in the 30-35% range. The beads were subjected to a screening operation to determine the yield and harvest those particles in the 8×16 U.S. mesh size range. The product beads were air dried overnight prior to calcination using a shallow tray method at temperatures up to 595° C. The shallow tray calcination method used a General Signal Company Blue-M electric oven equipped with a dry air purge. ~500 g. dry wt. of the 8×16 U.S. mesh adsorbent was spread out in a stainless steel mesh tray to provide a thin layer. A purge of 200 SCFH of dry air was fed to the oven during calcination. The temperature was set to 90° C., followed by a 6 hour dwell time. The temperature was then increased to 200° C. gradually over the course of a 6 hour period, and further increased to 300° C. over a 2 hour period and finally increased to 595° C. over a 3 hour period and held there for 1 hour before cooling to 450° C. after which the adsorbent was removed, immediately bottled in a sealed bottle and placed in a dry nitrogen purged drybox. The calcined beads were rescreened to harvest those particles in the 8×16 U.S. mesh range. The TGA method was adopted for nitrogen rate screening but nitrogen and methane values used to determine rate selectivity were obtained using the Hiden gravimetric method.

TABLE 1

For 35% $N_2$ in feed to 20% $N_2$ in product at a recovery of 80% at 35 C.

| Material | Isosteric Heat of adsorption (kJ/mol) | Commercial BSF - (lbs/MMscfd feed) | Purity | Production |
|---|---|---|---|---|
| Clino TSM-140 | 31 | 14,000 | 93% | 0.87 |
| Tunable zeolite 4A | 11 | 12,000 | 92% | 1 |
| ETS-4* | 32* | 12,000 | 93% | 1 |

*Material properties estimated from Patent WO1999032222A1 and BASF for their commercially available ETS-4 by the trade name Molecular Gate available commercially from BASF using the isotherm data available and the LRC method to fit that data.

The tunable zeolite 4A adsorbent, and commercially available clinoptilolite (clino) TSM-140 from Steelhead Specialty Minerals were then tested in a bench scale breakthrough system and compared with the modeled performance for ETS-4. These breakthrough results were then used in a model to predict commercial performance. The results show very similar performance of tunable zeolite 4A according to the invention compared with thermally regenerated clino TSM-140 and ETS-4. The performance of tunable zeolite 4A was simulated for more than 2 weeks after cyclic steady state had been which occurred after 4 days, while the clino TSM-140 and ETS-4 performance declined more than 80% over the course of those 4 days.

We claim:

1. A pressure swing adsorption process for separating an $N_2$ impurity from a feed stream comprising at least methane and said $N_2$ impurity, said process comprising feeding the feed stream to an adsorbent bed at a pressure of from about 60 psig to 2000 psig, wherein said adsorbent bed comprises adsorbent having:
   i. An isosteric heat of adsorption of from about 5 kJ/mol to about 25 kJ/mol, as determined by the LRC method, for the $N_2$ impurity, and
   ii. an equivalent isosteric heat of adsorption for methane that is from about 50% to about 200% of the adsorbents isosteric heat of adsorption for $N_2$, wherein the adsorbent has a rate of adsorption for the $N_2$ impurity that is at least 5 times greater than the rate of adsorption for methane as determined by the Hiden method, and recovering said methane with a reduced a level of $N_2$ impurity.

2. The process according to claim 1 wherein said adsorbent has an isosteric heat of adsorption for methane that is from about 50 to about 125% of the adsorbent's heat of adsorption for $N_2$.

3. The process according to claim 2 where the feed stream may contain additional gas species such as ethane, propane, butane and hydrocarbons with more than 4 carbon atoms and may include adsorbents to remove said hydrocarbons.

4. A process according to claim 2 where the feed stream may contain additional gas species such as water, carbon dioxide or sulfur species and may include adsorbents to remove said species.

5. The process of claim 1 wherein said adsorbent is selected from zeolite A, chabazite, mordenite, clinoptilolite, ZSM-5, or combinations thereof.

6. The process of claim 5 wherein the adsorbent is a zeolite exchanged with one or more cations selected from Li, Na, K, Mg, Ca, Sr, Ba, Cu, Ag, Zn, $NH_4^+$ and combinations or mixtures thereof.

7. The process of claim 1 wherein said adsorbent is Zeolite A.

8. A pressure swing adsorption process for separating $N_2$ from a methane gas feed stream said process comprising feeding the methane gas feed stream to an adsorbent bed at a pressure of from about 60 psig to 2000 psig, wherein said adsorbent bed comprises adsorbent having:

a heat of adsorption of from about 5 kJ/mol to about 25 kJ/mol, as determined by the LRC method, for the $N_2$ adsorbate, and
an isosteric heat of adsorption for methane that is from about 50 to about 200% of the adsorbents steric heat of adsorption for $N_2$, wherein the adsorbent has a rate of adsorption for $N_2$ that is at least 6 times greater than the rate of adsorption for methane as determined by the Hiden method and recovering said methane with a reduced a level of $N_2$.

9. The process according to claim 8 where the feed stream may contain additional gas species such as ethane, propane, butane and hydrocarbons with more than 4 carbon atoms and may include adsorbents to remove said hydrocarbons.

10. The process according to claim 8 where the feed stream may contain additional gas species such as water, carbon dioxide or sulfur species and may include adsorbents to remove said species.

11. The process of claim 8 wherein the feed gas temperature, product gas temperature and bed temperatures range from about 0° C. and 65° C.

12. The process of claim 8 wherein the feed gas temperature, product gas temperature and bed temperatures range from about 20° C. and 50° C. and the temperature during the process does not exceed 100° C.

13. The process of claim 8 wherein said adsorbent is selected from zeolite A, chabazite, mordenite, clinoptilolite, ZSM-5, or combinations thereof.

14. The process of claim 13 wherein said adsorbent is a zeolite exchanged with at least one cation selected from Li, Na, K, Mg, Ca, Sr, Ba, Cu, Ag, Zn, $NH_4^+$ and combinations or mixtures thereof.

15. The process of claim 8 wherein said adsorbent is Zeolite A.

16. An adsorbent for the separation of $N_2$ from a methane containing gas stream, said adsorbent having:
   An isosteric heat of adsorption of from about 5 kJ/mol to about 25 kJ/mol, as determined by the LRC method, for $N_2$ and
   an isosteric heat of adsorption for methane that is from about 50 to about 200% of the adsorbent's steric heat of adsorption for $N_2$, and wherein the adsorbent has a rate of adsorption for $N_2$ that is at least 6 times greater than the rate of adsorption for methane as determined by the Hiden method.

17. The adsorbent of claim 16 which comprises zeolite A, chabazite, mordenite, clinoptilolite, ZSM-5, or combinations thereof.

18. The adsorbent of claim 17 wherein said zeolites is exchanged with cations selected from Li, Na, K, Mg, Ca, Sr, Ba, Cu, Ag, Zn, $NH_4^+$ and combinations or mixtures thereof.

19. The adsorbent of claim 16 wherein said adsorbent is Zeolite A.

* * * * *